United States Patent [19]
Ando et al.

[11] Patent Number: 5,307,155
[45] Date of Patent: Apr. 26, 1994

[54] SAMPLE CHAMBER FOR A SPECTRO PHOTOMETER

[75] Inventors: Osamu Ando; Katsumi Harada, both of Kyoto, Japan

[73] Assignee: Shimadzu Corp., Kyoto, Japan

[21] Appl. No.: 830,364

[22] Filed: Jan. 31, 1992

[30] Foreign Application Priority Data

Jan. 31, 1991 [JP] Japan .................. 3-010264

[51] Int. Cl.$^5$ .................................... G01N 21/01
[52] U.S. Cl. .................... 356/430; 356/244; 356/435
[58] Field of Search ........... 356/319, 429, 430, 435, 356/443, 244; 250/559, 562, 571

[56] References Cited

U.S. PATENT DOCUMENTS

| | | | |
|---|---|---|---|
| 3,361,025 | 1/1968 | Gaffard | 250/571 |
| 3,563,667 | 2/1971 | Koskimines et al. | 356/429 |
| 3,841,761 | 10/1974 | Selgin | 356/430 |
| 4,848,904 | 7/1989 | Sapp et al. | 356/319 |

FOREIGN PATENT DOCUMENTS

| | | | |
|---|---|---|---|
| 1130197 | 5/1962 | Fed. Rep. of Germany | 356/319 |
| 215923 | 9/1988 | Japan | 356/319 |
| 215924 | 9/1988 | Japan | 356/319 |

*Primary Examiner*—Richard A. Rosenberger
*Attorney, Agent, or Firm*—Thomas R. Morrison

[57] ABSTRACT

A spectro photometer deflects a measuring beam off its original axis to pass through a long sample, and returns the measuring beam to its final direction after passing through the sample. The sample is guided along a path which is clear of a reference beam of the spectro photometer. This arrangement permits double-beam measurement of long samples, with good signal-to-noise ratio. Deflection is accomplished using a plurality of mirrors.

9 Claims, 5 Drawing Sheets

SAMPLE CHAMBER FOR A SPECTRO PHOTOMETER

BACKGROUND OF THE INVENTION

The present invention relates to spectro photometers and, more specifically, to an accessory device for use with a spectro photometer to measure the optical characteristics of long, solid materials shaped like a film or plate.

Spectro photometers are employed to measured the spectral transmittance or absorbance ratio of liquid and solid materials at varying wavelengths. The chemical and other characteristics of the materials are inferred from the measured spectrum for qualitative or quantitative analysis of the materials.

A holding apparatus holds the sample or container in a stable position during analysis. Liquid samples are generally held in a standardized container such as, for example, a test tube. Thus, a single holder design suffices to hold most liquid specimens during measurement. Solid materials present a different problem since they occur in different shapes and sizes which must be accommodated by a holder for holding the samples in place in the spectro photometer.

Unlike liquid media, which can be transferred into any common liquid medium container and placed within the optical path of the spectro photometer for analysis, the need for an apparatus to hold solids has prompted the development of several sample holders of different shapes and sizes, including spheres, plates, and rods.

A particular problem, to which the present invention is addressed, is holding long thin, flexible materials such as photographic film or magnetic tape. Also of relevance to the present invention is apparatus for holding glassware used in reflective mirrors for photocopiers. These samples are analyzed by spectro photometers to insure that the chemicals which coat the samples are uniformly distributed. The optical characteristics of these materials are calculated as a function of the distance from an emitted beam as the sample is moved through the optical path of the incident beam. Due to the relatively small size of a typical spectro photometer, however, there is very little space available for a sample holder or its sample.

Prior art spectro photometers employ two parallel beams of light: a measuring beam and a reference beam. Conventionally, both beams are split from the same light source. The measuring beam passes through the sample whose optical properties are being measured while the reference beam passes through a reference sample with known chemical characteristics. After the measuring beam emerges from the sample, the beams are compared for changes in intensity and wavelength. The use of two beams in this manner is termed "double beam measurement". The presence of the reference beam permits cancelling out changes in the received measuring beam due to systematic changes in source brightness.

A difficulty emerges when using double beam measurement for analyzing long, flat, solid samples. The geometry of a conventional spectro photometer is such that, when performing measurements on, a long object such as, for example, a glass rod, the rod intercepts the reference beam, as well as the measuring beam. As a result of this problem, when measuring long solid objects, only the measuring beam can be used in the analysis. The reference beam is turned off, blocked or ignored. This so-called "single beam measurement" is not as accurate as double beam measurement, since the source brightness of light sources of spectro photometers are subject to an inherent drift with power supply voltage and lamp age which is normally compensated for by the reference beam.

When analyzing a flat sample of film, the flexibility of the material allows it to be fed through the spectro photometer on a bent path which avoids interference with the reference beam. In one prior-art device, the film is fed into the spectro photometer through an inlet above the optical bath of the measuring beam. A film guide directs the film through the optical path of the measuring beam and sends it on a skewed path to an outlet. The inlet and outlet are separated by an offset distance large enough to prevent the film from crossing the optical path of the measuring beam twice, yet small enough to keep the film out of the path of the reference beam. Since the reference beam is unaffected, double beam measurement can be used.

Achieving double beam measurement for film in this manner is not without its disadvantages. First, the presence of the equipment which feeds and winds the film above the sample chamber makes it difficult to access the chamber through a simple cover. Second, the curved shape of the film guide make it difficult and expensive to produce. Also, the area of the film measured by the spectro photometer is not ideal.

The above prior-art device also suffers from a decrease in signal-to-noise ratio. Before reaching the film, the measuring beam must pass through a beam diaphragm to increase the resolution of the spectro photometer measurements. The opening in the diaphragm is rectangular in shape, and the base must extend the width of the film. The base in the horizontal plane is thus much longer than the side in the vertical plane. The measuring beam, however, is rectangular in shape with the base in the horizontal plane much smaller than the side in the vertical plane. The result is two overlapping rectangles at right angles to each other wherein a major part of the measuring beam is blocked by the diaphragm, resulting in a corresponding degradation in signal-to-noise ratio.

OBJECTS AND SUMMARY OF THE INVENTION

Accordingly, it is the object of the present invention to provide a spectro photometer that measures long samples using double beam measurement.

A further object of the present invention is to provide a spectro photometer which can employ double beam measurement with improved signal-to-noise ratio.

It is a still further object of the invention to provide a spectro photometer which includes a sample holder capable of feeding a long sample past a sample beam without intercepting a reference beam.

It is a still further object of the invention to provide a spectro photometer which includes apparatus for deflecting a sample beam out of its original path through a sample, and for returning the sample beam to continue on its original path.

Briefly stated, the present invention provides a spectro photometer that deflects a measuring beam off its original axis to pass through a long sample, and returns the measuring beam to its final direction after passing through the sample. The sample is guided along a path which is clear of a reference beam of the spectro photometer. This arrangement permits double-beam measurement of long samples, with good signal-to-noise ratio. Deflection is accomplished using a plurality of mirrors.

In the above system, the sample is placed either above or below the horizontal plane formed by the measuring beam and the reference beam, with the optical system aligned accordingly. Since the sample no longer blocks the optical path of the reference beam (which prompted single beam measurement in the prior art), double beam measurement can be employed.

When designing the configuration of the optical system, the amount of noise which affects the analysis of the spectro photometer is negligible, even though the measuring beam is longer and stronger than that of the prior art.

According to an embodiment of the invention, there is provided a spectro photometer with a sample chamber of a type having a measuring beam and a reference beam, comprising: the measuring beam having a first initial direction and a first final direction, the a reference beam having a second initial direction and a second final direction, the second the initial direction being generally parallel with the first initial direction, a guide for guiding an object to be measured, means for redirecting one of the measuring beam and the reference beam out of its initial direction, the means for redirecting including means for permitting the measuring beam to pass through the object without blocking the reference beam with the object, and means for directing the measuring beam and the reference beam in their final directions.

According to a feature of the invention, there is provided a spectro photometer for use with a measuring beam and a reference beam comprising: initial paths of the measuring beam and the reference beam defining a plane, a sample guide disposed parallel to the plane, but displaced outside the plane, means for redirecting the measuring beam out of its initial path through a sample in the sample guide, and means for passing the reference beam and the measuring beam, after it passes through the sample, to a measuring section, whereby dual-beam measurements of the sample can be carried out.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 5:
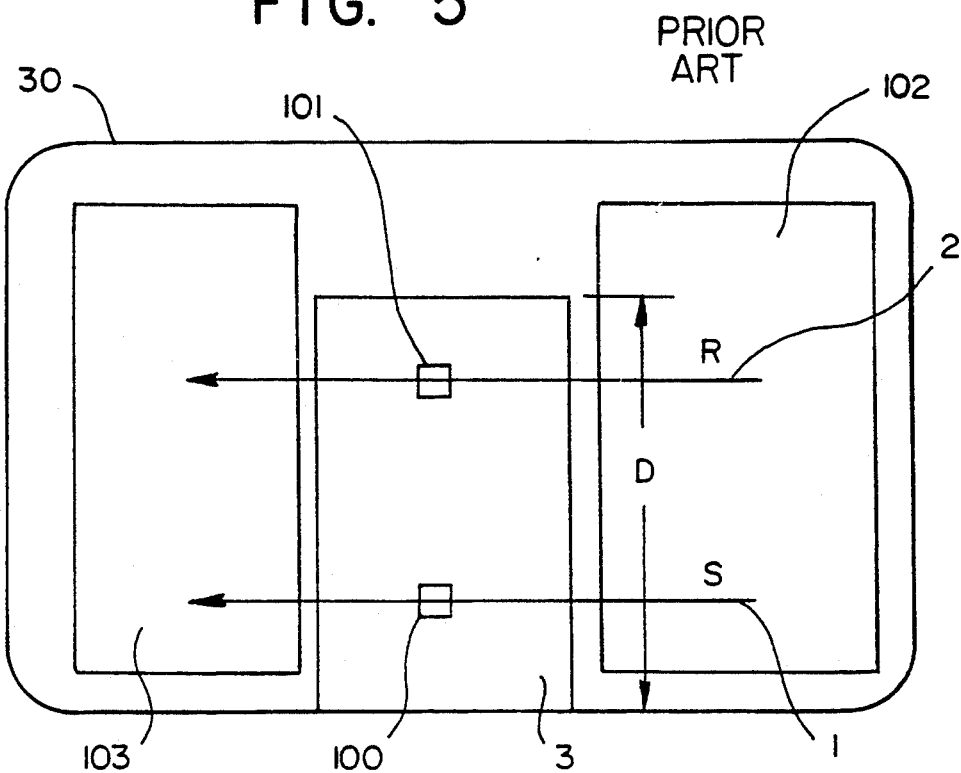
FIG. 5 is a simplified schematic diagram of a dual-beam spectro photometer according to the prior art.

Referring to the prior art in FIG. 5, a spectro photometer 30 contains an emitter section 102 which emits a measuring beam 1 and a reference beam 2. Measuring beam 1 and reference beam 2 originate in the same light source (not shown) which is spectrally scanned before being split into the two beams 1 and 2. Thus measuring beam 1 and reference beam 2 are identical. A sample holder 3 contains a measuring sample holder 100 and a reference sample holder 101. Measuring beam 1 passes through an unknown sample in measuring sample holder 100, whose, optical properties are to be measured. After passing through measuring sample holder 100, measuring beam 1 enters a measuring section 103. Similarly, reference beam 2 passes through a reference sample, held in reference sample holder 101, before entering measuring section 103. Since measuring beam 1 and reference beam 2 initially are identical, any difference in these beams as they enter measuring section 103 is due to differences in optical properties of the contents of measuring sample holder 100 and reference sample holder 101. Such "double beam measurement" is used in measuring section 103 to compensate for variations in light-source intensity and color temperature.

The apparatus of FIG. 5 is especially useful for liquid samples which can be contained in sample holders of rectangular cross section. In some applications, reference sample holder 101 may be omitted, whereby reference beam passes directly into measuring section 103.

Figure 6:
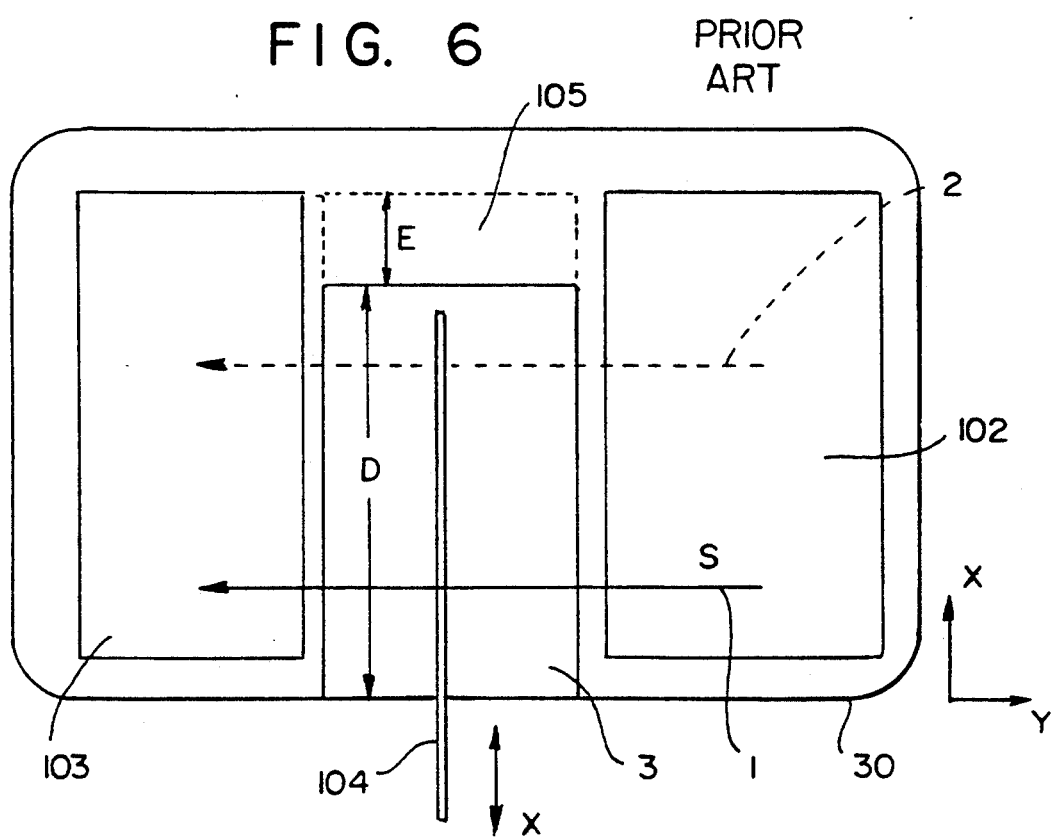
FIG. 6 is a plan view of the prior-art single-beam spectrometer of FIG. 5.

Referring now to the prior art in FIG. 6, a rigid long object 104 is placed sample holder 3 in a manner which allows the long object 104 to move in the X direction through the optical path of measuring beam 1. Due to its length, however, long object 104 can move far enough in sample holder 3 to intercept the path of reference beam 2. This interferes with using reference beam 2. Accordingly, reference beam is turned off, blocked or distarted.

Even accommodating long object 104 by foregoing double-beam measurement does not solve all of the problems. In the ideal, it would be desirable to accommodate a long object 104 of any desired length. However, the depth of sample holder 3 of conventional spectro photometer 30 limits the length of long object 104 which can pass through measuring beam 1 to a depth D. In some cases, an additional depth E may be made available in an expansion area 105. This is a severe limit for some applications where long transparent objects such as glass rods or long optical components are to be measured.

Figure 7:
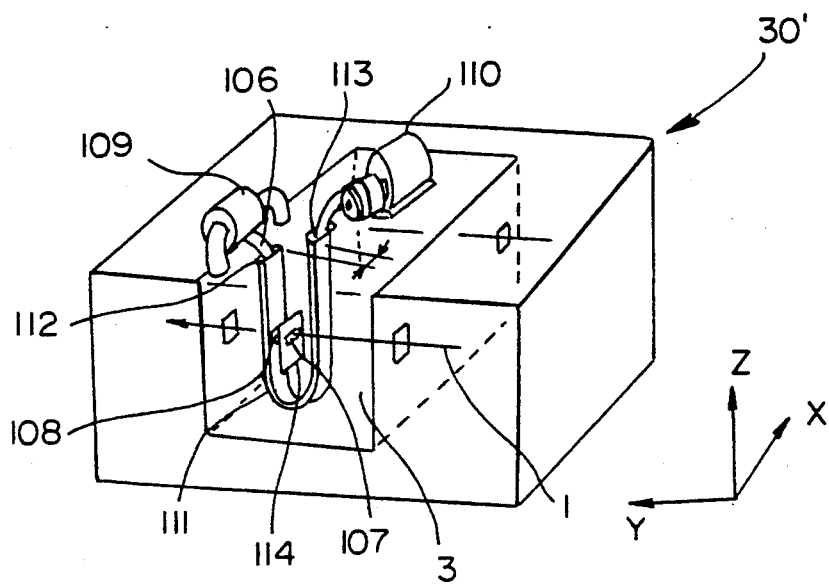
FIG. 7 is a perspective diagram of a spectro photometer according to another example of the prior art.

Referring FIG. 7, a further spectro photometer 30', according to the prior art includes a film cartridge 109 capable of holding a film 106 and feeding it through an inlet 112 into a film guide 111 in spectro photometer 30'. Film guide 111 guides film 106 on a downward run that passes through measuring beam 1, and then guides it upward on a skewed path to an outlet 113, before it is finally reeled up on a film spool 110.

The folded path produced by film guide 111 moves film 106 in a path that avoids blocking the optical path of reference beam 2, thus permitting double beam measurement to be used. The folded path also permits feeding a film 106 of any length through spectro photometer 30'.

Achieving double beam measurement for film 106 in this manner, however, is not without its disadvantages.

Accommodating film cartridge 109 and film spool 110 prevents the use of a simple cover to allow easy access to the internal mechanism. A large, bulky cover which envelops the entire surface of sample holder 3 is thus required.

Inlet 112 and outlet 113 are separated by an offset distance d. This distance and the shape of film guide 111 provides the skew that permits measuring beam 1 to pass through film 106, without blocking the optical path of measuring beam 1 except at spot 108. The unusual shape of film guide 111, however, makes it difficult and expensive to produce.

Before reaching film 106, measuring beam 1 passes through a beam diaphragm 114, which increases the resolution of the device by adjusting the beam diameter through a rectangular beam outlet 107. The base of rectangular beam outlet 107 approximately matches the width of film 106.

Figure 8:
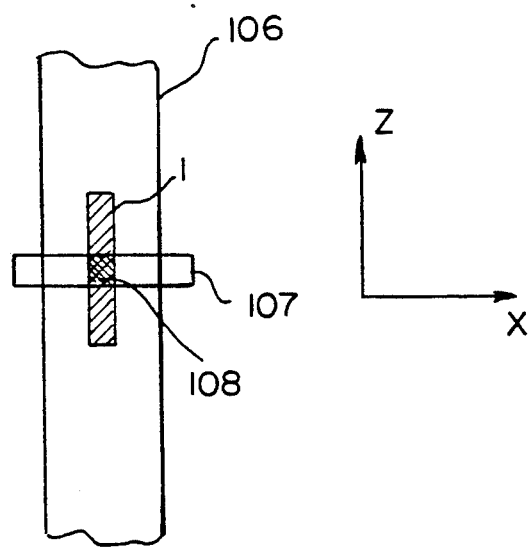
FIG. 8 is a schematic diagram of the beam shape on a beam diaphragm in the spectro photometer of FIG. 7.

Referring now also to FIG. 8, the base of beam outlet 107 is thus much longer in the X direction than in the Z direction. Measuring beam 1, however, is rectangular with its side much longer in the Z direction than its base in the X direction. The different orientations of measuring beam 1 and beam outlet 107 produce spot 108 only where the two thin rectangles intersect each other. Most of measuring beam 1 is blocked by diaphragm 114, thus resulting in an a weak measuring beam and a decrease in signal-to-noise ratio.

Figure 1:
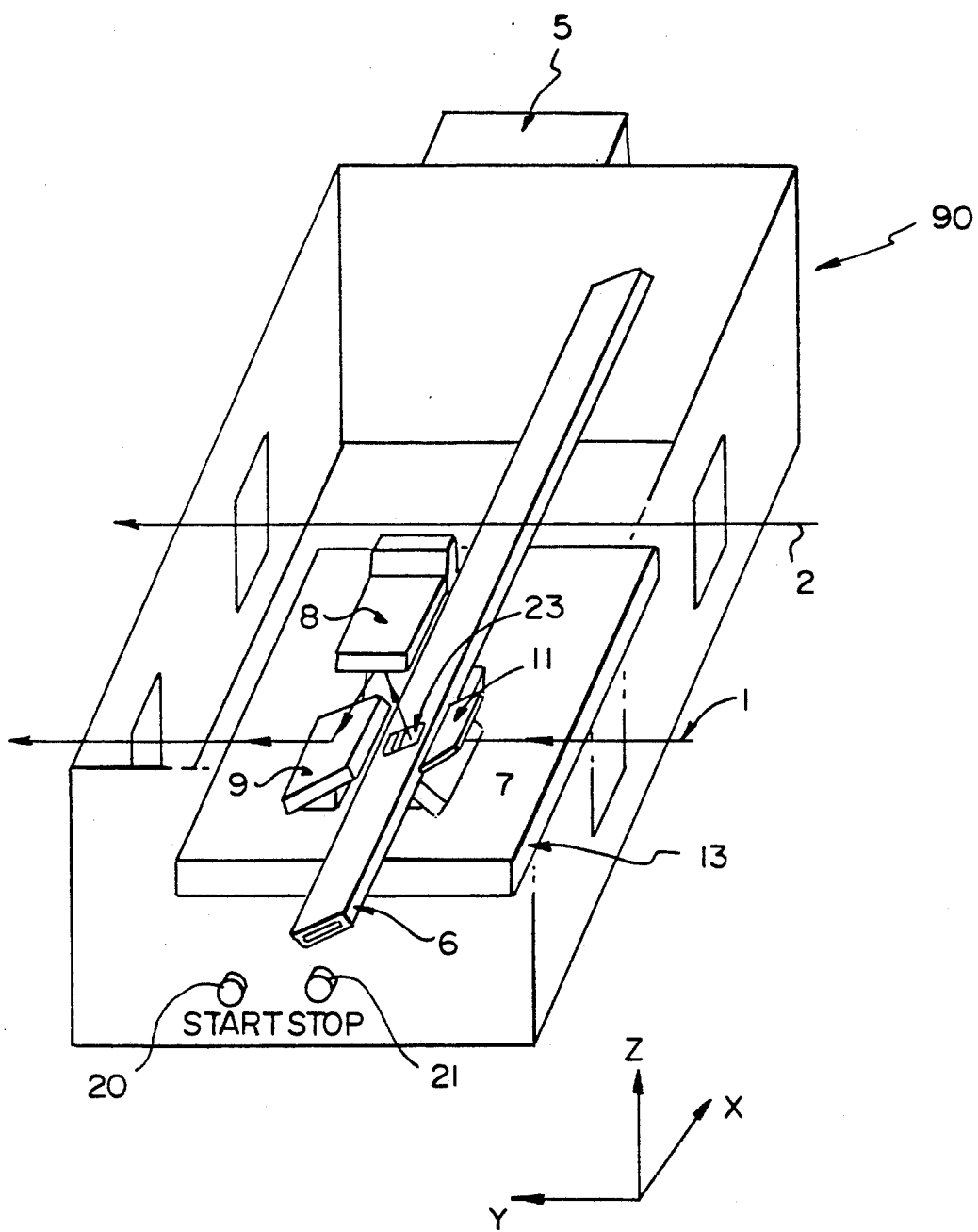
FIG. 1 is a perspective diagram of a spectro photometer according to an embodiment of the invention.

Referring now to FIG. 1, a sample chamber 90 according to the present invention permits a film guide 6 to pass in a straight path along an X axis off the direct paths of both measuring beam 1 and reference beam 2. Film guide 6 is inclined at an angle of about 60 degrees to a horizontal plane. An opening 23 in film guide 6 permits the passage therethrough of measuring beam 1, as is described below.

Figure 2:
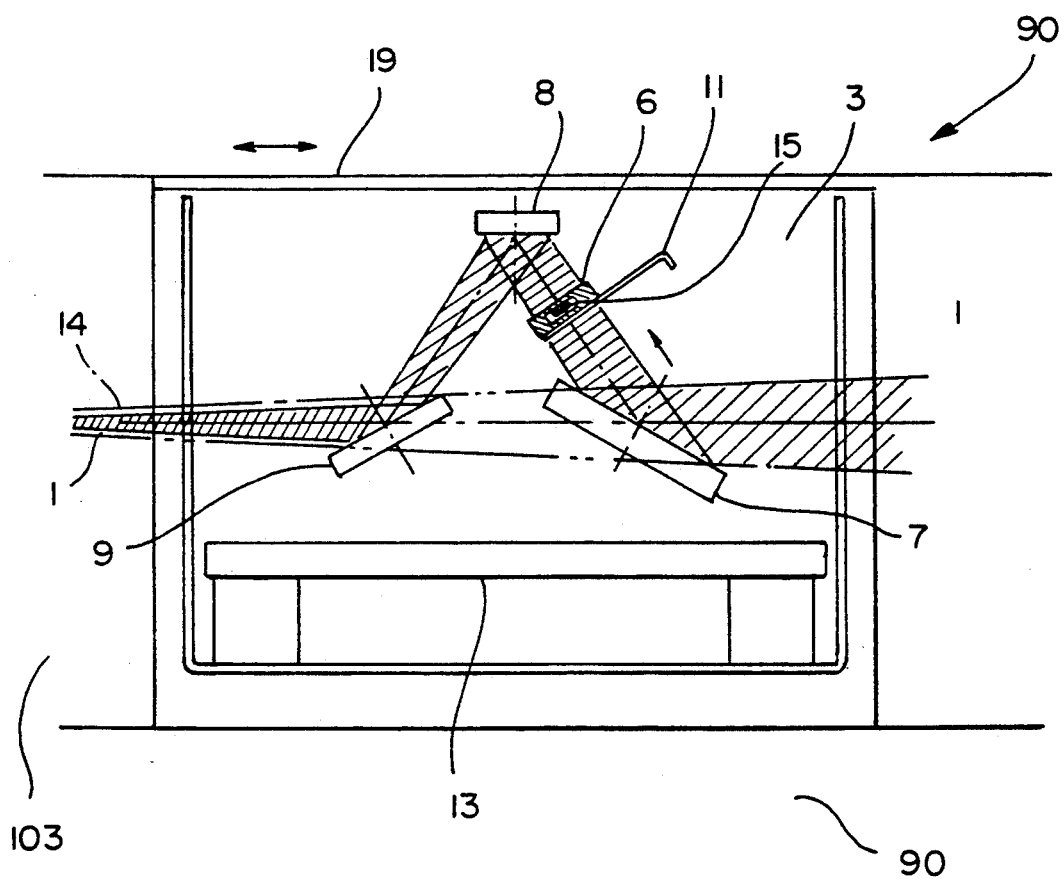
FIG. 2 is a front view of the spectro photometer of FIG. 1.

Referring now also to FIG. 2, an optical system, including mirrors 7, 8 and 9, deflect measuring beam 1 about 150 degrees off its original path, and through opening 23 approximately at right angles to the plane of a film 15 being guided in film guide 6. After passing through opening 23, measuring beam 1 is returned to its original path by reflection from mirrors 8 and 9. Each reflective mirror 7, 8 and 9 is supported by individual support devices, and a base 13 supports the entire system. See also FIG. 2.

It will be evident to one skilled in the art that the path of measuring beam 1, being deflected by mirrors 7, 8 and 9, is longer than it would be without the deflection. As shown, measuring beam 1 is a converging beam. If it were not deflected, measuring beam 1 would have an original beam width 14 as it enters measuring section 103. Due to the increased path length, however, the width of measuring beam 1, as it enters measuring section 103 is reduced as shown.

A film guide 6, which is designed according to the dimensions and slidability of film 15, continuously leads film 15 through the path of measuring beam 1. Film guide 6 is located on the optical path between reflective mirrors 7 and 8 and extends the length of sample chamber 90. Due to its inclination 60 degrees off the horizontal plane, and the inclination of mirror 7, measuring beam 1 passes approximately perpendicularly through film 15.

Figure 3:
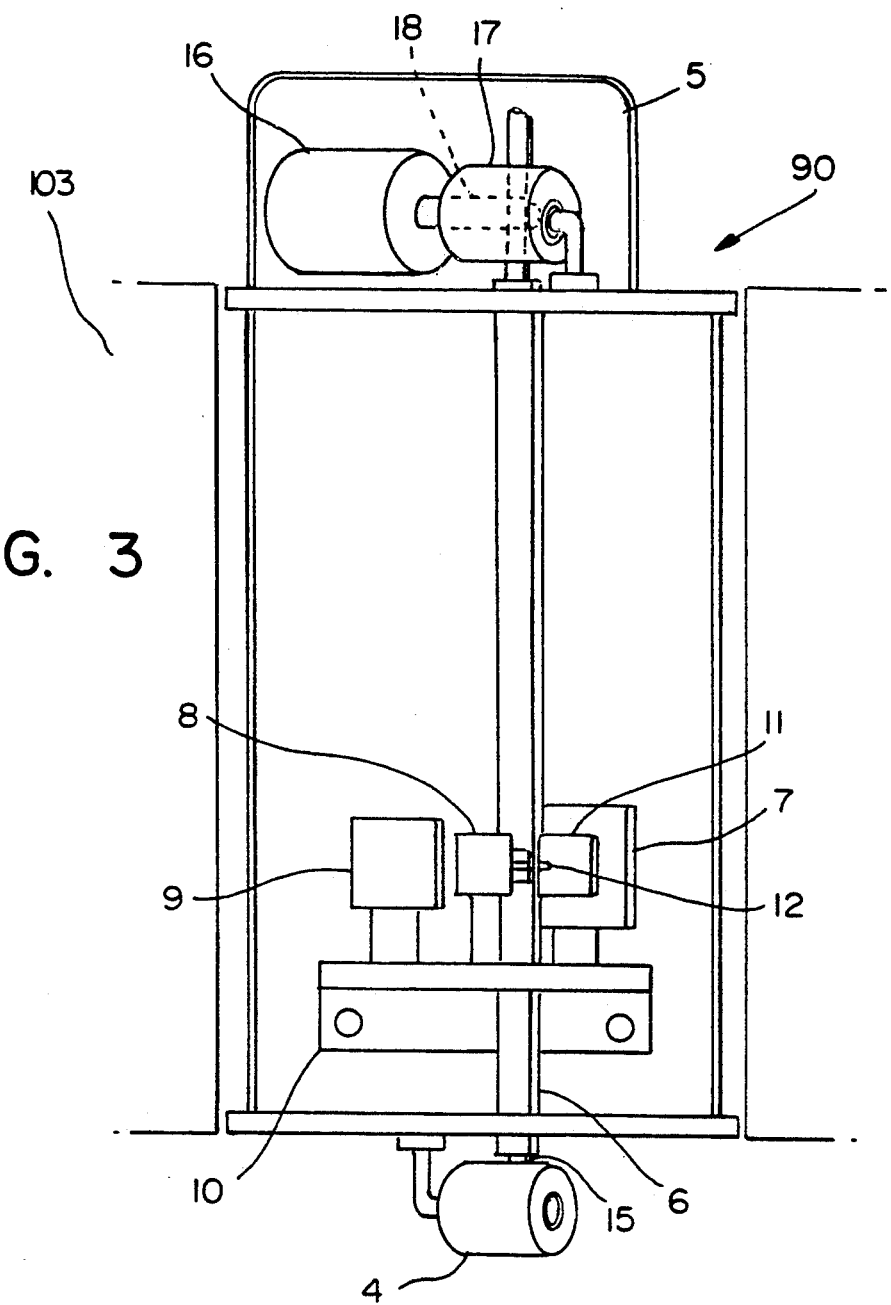
FIG. 3 is a plan view of the spectro photometer of FIG. 1

Referring now to FIG. 3, film 15 is fed from a cartridge 4, located on the front of sample chamber 90, and pulled through film guide 6. The end of film 15 is wound in a film winding section 5, which includes a motor 16, a pinch roller 17 and a capstan roller 18. Pinch roller 17 is held in contact with pinch roller 17, with film 15 therebetween, by a spring system (not shown).

Referring again to FIG. 1, motor 16 continuously pulls film 15 through measuring sample chamber 90 with a fixed tension. Button switches 20 and 21 control the operation of motor 16, which is connected electrically with a control section of spectro photometer 30 (not shown).

Since film guide 6 is located off the horizontal plane defined by beams 1 and 2, film guide 6 does not block the optical path of reference beam 2. For measuring long flexible objects, such as film 15, the present invention simplifies the guide, and positions film 15 to permit minimum blockage of measuring beam 1, and thereby to provide maximum signal-to-noise ration.

Figure 4:
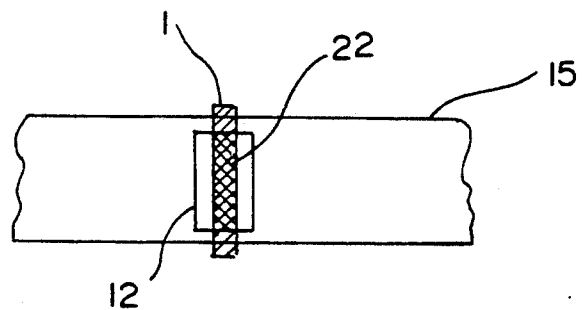
FIG. 4 is a schematic diagram of beam shape on a measuring section in a spectro photometer of the invention.

Referring now to FIG. 4, a beam diaphragm 12, which is placed in a small recess of film guide 6, restricts the diameter of the beam to increase the measurement resolution. Since the film moves in the X direction (rather than the Z direction of the prior art), the length of the base of diaphragm is parallel to the side of the rectangular shape of measuring beam 1. Unlike the prior art, where the two rectangles at right angles caused a loss of the majority of measuring beam 1 and created a large amount of noise, here only a small portion of measuring beam 1 is filtered, thus producing a large spot 22 with higher energy and negligible noise.

With the removal of film cartridge 109 and film spool 110, a simple cover 19, which slides back and forth in the X direction, can be placed in the top of sample chamber 90. This allows easy access to the internal optical system.

When long rigid objects are to be measured, film guide 6 is replaced by a guide (not shown) suitable for the object to be measured. The long rigid object is passed along the same path as that occupied by film 15, off the direct axis of beams 1 and 2. As a consequence, double beam measurement can be used even with long rigid objects that would otherwise block reference beam 2.

Instead of redirecting measuring beam 1, as described in the preceding, corresponding results can be obtained by placing film guide 6 in the direct path of measuring beam 1, and optically displacing reference beam 12 off its original path to avoid blockage thereof. The same system could be used to redirect the reference beam. Redirecting reference beam 1 produces a similar result with long rigid samples.

The present invention as above permits measurement of the spectral transmittance and reflectivity of long samples such as a film or glass using double beam measurement, which is more accurate than single beam measurement.

The present invention also improves the accuracy and stability of the measurements of the spectro photometer, since it employs a beam of higher energy than the prior art with the same resolution. Cover 19 on sample chamber 90 requires no modification, and thus allows easy access to the internal optical system. This improves ease of adjustment and maintenance, thus producing higher productivity and efficiency.

It would be clear to one skilled in the art that, although the foregoing disclosure is directed to the use of reflective optics for redirecting measuring beam 1, corresponding result are obtainable using refractive optics. In addition, although the above description defines the redirection of measuring beam 1, corresponding results would occur by redirecting reference beam 2 from its initial direction to avoid interception by the sample. Both of these alternatives should be considered to be within the spirit and scope of the invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A spectro photometer with a sample chamber of a type having a measuring beam and a reference beam, comprising:
   said measuring beam having a first initial direction and a first final direction;
   said a reference beam having a second initial direction and a second final direction;
   said second said initial direction being generally parallel with said first initial direction;
   a sample guide adapted for guiding a long flat sample to be measured;
   means for redirecting one of said measuring beam and said reference beam out of a respective one of said first and second initial direction;
   said means for recdirecting including means for permitting said measuring beam to pass through said object without blocking said reference beam with said object;
   said sample guide including means for passing light therethrough;
   said means for passing light including an opening;
   said measuring beam having a cross-sectional expanse;
   a first axis of said opening and a second axis of said cross-sectional expanse of said measuring beam being disposed in a common direction to minimize degradation of a signal to noise ratio; and
   means for directing the redirected one of said measuring beam and said reference beam in a respective one of said first and second final direction.

2. Apparatus according to claim 1 further comprising;
   means for inclining said sample at right angles to said measuring beam; and
   said sample guide being located out of the optical paths of said measuring beam and said reference beam.

3. Apparatus according to claim 1, wherein said means for redirecting includes at least one mirror.

4. Apparatus according to claim 1, wherein said at least one mirror includes a plurality of mirrors.

5. An apparatus according to claim 1, further comprising:
   a first winding reel for dispensing said long flat sample into said guide; and
   a second winding reel for collecting said long flat sample from said guide.

6. A spectro photometer for use with a measuring beam and a reference beam comprising:
   initial paths of said measuring beam and said reference beam defining a plane;
   a sample guide disposed parallel to said plane, but displaced outside said plane;
   said sample guide including means for accommodating a long flat sample;
   means for redirecting said measuring beam out of its initial path through a sample in said sample guide;
   said sample guide including means for passing light therethrough;
   said means for passing light including an opening;
   said measuring beam having a cross-sectional expanse;
   a first axis of said opening and a second axis of said cross-sectional expanse of said measuring beam being disposed in a common direction to minimize degradation of a signal-to-noise ratio produced when said measuring beam passes through said sample guide; and
   means for passing said reference beam and said measuring beam, after it passes through said sample, to a measuring section, whereby dual-beam measurements of said sample can be carried out.

7. A sample chamber for a spectrophotometer having first and second beams of light, comprising:
   said first beam having a first initial direction and a first final direction;
   said second beam having a second initial direction and a second final direction;
   said first and second initial directions defining a plane therebetween;
   at least a first flat mirror for directing one of said first and second beams out of said plane;
   means for guiding a long flat sample;
   said means for guiding having an opening;
   said means for guiding being disposed to permit said first beam to pass through said opening without blocking said second beam;
   at least a second flat mirror for redirecting the directed one of said first and second beams into its respective final direction.

8. A sample chamber for a spectrophotometer having a measuring beam and a reference beam, comprising:
   said measuring beam having an initial direction and a final direction;
   a first mirror for reflecting said measuring beam;
   means for guiding a long flat sample;
   said means for guiding being disposed out of a plane formed by said reference beam and said measuring beam;
   said means for guiding being disposed within the volume enclosed by the spectrophotometer;
   said means for guiding having an opening for receiving said measuring beam;
   said means for guiding being disposed at an angle substantially perpendicular to said measuring beam after reflecting off said first mirror; and
   at least a second mirror for redirecting said measuring beam into said final direction.

9. An apparatus according to claim 8, further comprising:
   said first flat mirror being flat; and
   said at least a second mirror being flat.

* * * * *